United States Patent
Schmidt et al.

(10) Patent No.: US 7,001,606 B2
(45) Date of Patent: Feb. 21, 2006

(54) BIOCIDAL POLYMERS BASED ON GUANIDINE SALTS

(75) Inventors: Oskar J. Schmidt, Vienna (AT); Andreas Schmidt, Reinach/BI (CH); Dimitri Toptchiev, Moscow (RU)

(73) Assignee: P.O.C. Oil Industry Technology Beratungsges m.b.H., Vienna (AT)

( * ) Notice: Subject to any disclaimer, the term of this patent is extended or adjusted under 35 U.S.C. 154(b) by 582 days.

(21) Appl. No.: 10/275,124

(22) PCT Filed: May 8, 2001

(86) PCT No.: PCT/AT01/00134
§ 371 (c)(1),
(2), (4) Date: Oct. 31, 2002

(87) PCT Pub. No.: WO01/85676
PCT Pub. Date: Nov. 15, 2001

(65) Prior Publication Data
US 2003/0113291 A1  Jun. 19, 2003

(30) Foreign Application Priority Data
May 11, 2000 (AT) ............................... A 826/2000
Oct. 23, 2000 (AT) ............................ A 1818/2000

(51) Int. Cl.
*A01N 25/00* (2006.01)
*C08G 12/00* (2006.01)
*C08G 63/00* (2006.01)
*C08G 69/26* (2006.01)

(52) U.S. Cl. .................. 424/405; 424/400; 528/125; 528/128; 528/172; 528/173; 528/183; 528/220; 528/229; 528/332; 528/350; 528/353

(58) Field of Classification Search ............... 424/405, 424/400; 528/125, 128, 172, 173, 183, 220, 528/229, 332, 350, 353
See application file for complete search history.

(56) References Cited

U.S. PATENT DOCUMENTS 6,008,316 A * 12/1999 Foster et al. ................ 528/229

* cited by examiner

*Primary Examiner*—Thurman K. Page
*Assistant Examiner*—Simon J. Oh
(74) *Attorney, Agent, or Firm*—Herbert Dubno

(57) ABSTRACT

The invention relates to biocidal polymers based on guanidine salts characterized in that they are representatives of a number of polyoxyalkylene guanidines and their salts and are a product of a polycondensation of guanidine salts with diamines which include two amino groups and polyoxyalkylene chains therebetween.

In addition to a high bactericidity, these new polymer products are provided with a relatively low toxicity, an increased hydrophily, a quick and complete dilution in water, increased values of relative molar mass, and distinct characteristics of polymer surface active substances.

9 Claims, No Drawings

BIOCIDAL POLYMERS BASED ON GUANIDINE SALTS

The invention relates to biocidal polymers based on guanidine salts which are used as disinfectants in medicine, veterinary medicine, sewer treatments, households, and all branches of the economy which require biocidal preparations. Additionally, the invention relates to a process for producing such salts.

The purpose of the present invention is the production of a homogenous and pure disinfectant of a high molecular weight based on guanidine salts being provided with low toxicity but with a highly biocidal activity, a greater relative molar mass, a higher hydrophily, and the characteristics of surface active substances.

This is attained in the guanidine derivatives being a product of polycondensation of a guanidine acid addition salt and diamines containing two amino groups and polyalkylene chains therebetween.

The production of this product occurs according to the invention such that the liquid diamines are exposed to the polycondensation with guanidine salts in a medium of liquid diamines permanently being thoroughly mixed from the beginning of the reaction to its completion at a raised temperature and the duration of the polycondensation being in the range of 9–16 hours, depending on the type of diamine used.

According to the present invention the performance of the reaction is ensured in a liquid phase under permanent thorough mixing from the beginning to the completion in the range of the synthesis. Thus, the required homogenization of the systems, the observation of the required mol relations of the reagents during the process of the reaction, i.e., a high quality of the product, the facilitation of the technical equipment for the process and a facilitation of the security requirements demanded from such a process are provided.

In particular, triethylene glycol diamine having a relative molar mass of 148 and polyoxyalkylene diamines of various compositions are processed with the guanidine acid addition salts. Here, a large number of biocidal polymers of a polycationic nature can be produced having a high activity and a low toxicity. These polymers can be used practically as disinfectants for various purposes.

Salts of inorganic and organic acids are examples for the guanidine acid addition salts suitable for the performance of the polycondensation reaction of triethylene glycol diamine with polyoxyalkylene diamines, such as hydrochlorides, dihydrogen phosphates, carbonates, sorbates, nitrates, hydroacetates, gluconates, citrates, and silicates.

The suggested diamines are liquids having a high level of hydrophily, a low volatility, and a relatively low vapor pressure ensuring that no diamine vapors are present during the reaction process, neither in the reaction apparatus nor in the environment, and that no changes in the molar relations of the reagents occur during the reaction process. The utilization of the listed diamines allows the thorough mixing in a liquid reaction medium from the beginning of the reaction to its completion, i.e., an effective control of the process.

The reaction preferably occurs at an original molar relation of the reagents guanidine salt and DA of 1:1 under permanent thorough mixing at temperatures ranging from 140° C. to 190° C. depending on the type of the diamine used. For the reaction a common, pure guanine salt (99% purity) is used. As a result, new polymer biocides are produced on the base of guanidine salt, the water-soluble polyoxyalkylene guanidine salts, which are provided with an increased bactericidity and a better level of hydrophily and prominent characteristics of polymer surface active substances. The value of minimum inhibitive concentration in % for $E.\,coli$ is 0.00008, i.e., it is considerably better than for PHMG; the relative molar mass Mw=13,500 is higher than for PHMG, the toxicity is lower, namely $LD_{50}$=3400 mg/kg for rats compared to PHMG having $LD_{50}$=2500 mg/kg.

The achieved results can be demonstrated using the following examples with the examples 1 through 4 being correspondent to the enclosed table:

EXAMPLE 1

At a room temperature of 20° C., 25,28 (0.17 Mol) liquid diamine-triethylene glycol diamine (TEDA) ($H_2N$—$CH_2CH_2$—O—$CH_2CH_2$—O—$CH_2CH_2$—$NH_2$) is filled into a three-necked piston having a capacity of 250 ml and being provided with a mixing device and an air cooler. Subsequently, 16.34 g (0.17 Mol) of powdered guanidine hydrochloride (GHCl) is inserted into the piston. Under permanent thorough mixing the piston is heated to a temperature of 150° C. for the duration of 5 hours. Depending on the progression of the reaction, the viscosity of the reaction medium increases parallel to the release of ammonia in the form of a gas. A probe was taken from the reaction apparatus in this state of the process. This resinous, yellow product is hydrophilic and quickly dilutes in water in its entirety. The weighted-in quantity of the dried sample of this product (sample 1a) was diluted in water and its characteristic viscosity was measured using an Ubbelohde-viscosimeter. The result $[\eta]$=0.04 dl/g proves that, in this state of the reaction already, a polymer product is formed having an average weight of the relative molar mass Mw=2500. This product is already provided with biocidal characteristics (see table).

Subsequently, the heating continues for another 9 hours at a temperature of 170° C. simultaneously mixing the liquid reaction mixture thoroughly. Here, the gas development and the increase of the viscosity of the reaction medium continues as well. After the mentioned reaction time of 9 hours at a temperature of 170° C., another probe No. 1b) was taken from the reaction system. The color intensity of the polymer probe increased to a light brown. The measuring of the characteristic viscosity of this sample 1b) results in a value $[\eta]$=0.07 dl/g which correlates to an average weight of the relative molar mass Mw=5800, which means that the relative molar mass increases during the progression of the reaction. The bactericidity increases as well, see table. Since a gas development can still be observed after an exposure for the duration of 9 hours at a temperature of 170° C., i.e., the reaction was not completed, the heating of the reaction system was continued for another 4 hours at a temperature of 170° C. Subsequently, the development of gas and the reaction were completed.

Finally, another polymer sample 1c) was taken and its characteristic viscosity values were measured, $[\eta]$=0.085 dl/g, which corresponds to a relative molar mass of Mw=9100. The product of the reaction quickly dilutes in water in its entirety and is provided with a considerable hydrophily.

Determining the components of the separate elements of the polymer product resulted in the following:

It was determined in %: C-40,4; 40,25; N-19,7; 19,85; H-7.4; 7,456.

It was calculated for $C_7N_3O_2Cl\ H_{16}$ in %: C-40,1; N-20, 04; H-7,63.

Thus, a new polymer product was produced which corresponds in its composition to polytriethylene glycol guanidine hydrochloride. The final product of the experiment described is produced in a quantity yield of 98.7%. It is of low toxicity, the oral dose for rats is $LD_{50}$=3100 mg/kg, i.e., it is provided with a considerably lower toxicity than PHMG (see table) and a high bactericidal activity.

EXAMPLE 2

The same original ingredients are inserted into the reaction piston in the same amount and in the same mol relation as in example 1. Under permanent thorough mixing, the reaction occurs from the beginning to the completion at a temperature of 150° C. for the duration of 25 hours until no more ammonia is released. The reaction product achieved is water-soluble, has a light brown color, and a yield of 99.1%. The reaction product corresponds in the composition of its elements to polyethylene glycol guanidine hydrochloride.

Composition of the Elements

It was determined in %: C-40.7; N-19.65; H-7.6
It was calculated in %: C-40.01; N-20.04; H-7.63.

The characteristic viscosity of this sample (sample 2) was measured in [η]=0.11 (Mw=11800). This sample is provided with a higher bactericidal activity and a lower toxicity than PHMG (see table.)

EXAMPLE 3

In a three-necked piston having a capacity of 250 ml and being provided with a mixing device and an air cooler, 48 g (0.208 mol) liquid polyoxypropylene diamine is inserted at a room temperature of 20° C. having the following structure:

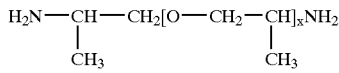

x = 2.6 has a molar weight of 230 and an equimolar amount of powdered guanidine hydrochloride (GHCl) of 19 g (0.208 mol). Under permanent thorough mixing, the mixture is heated, first for the duration of 2 hours at a temperature of 150° C., and then for the duration of 9 hours at a temperature of 170° C. In this state, the sample 3a) is taken from the reaction mixture, a hydrophile, sticky product of a light brown color, and its characteristic viscosity is measured: [η]=0.045 dl/g which corresponds to a molar weight Mw=3000. Furthermore, the heating is continued for the duration of another 9 hours at a temperature of 170° C. until no more ammonia is released, i.e., to the completion of the reaction. The yield of the final product is 98.9%.

According to the data of the analysis of the separate elements, the final product corresponds to the required formula of polyoxypropylene guanidine hydrochloride.

It was determined in %: C-50.85; N-13.35; H-9.6
It was calculated in %: C-50.4; N-13.57; H-9.69.

The characteristic viscosity of the final product of the reaction, the sample 3b) was determined [η]=0.12 which corresponds to a molar weight Mw—12500, i.e., it is higher than in the case of PHMG.

The determination of the bactericidity (E.coli: stock No. 2590) for sample 3b) has shown a higher biocidal activity and a lower toxicity in relation to PHMG (see table).

EXAMPLE 4

In a three-necked piston having a capacity of 250 ml and being provided with a mixing device and an air cooler, 124.8 g (0.208 mol) liquid diamine—polyoxyethylene diamine/polyoxypropylene—with a molar weight of 600 is inserted at a room temperature of 20° C. having the following structural formula:

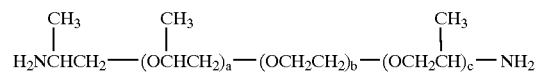

a+c=2.5, b=8.5 and 19 g (0.208 mol) guanidine hydrochloride (GHCl).

Furthermore, the reaction mixture was heated for the duration of 25 hours at a temperature of 150° C. under permanent thorough mixing. During the progression of the reaction a release of ammonia and an increase of viscosity of the reactional system occurred. After heating for the duration of 25 hours no more ammonia was released, i.e., the reaction was completed. A reaction product was produced at a yield of 99.1%. It is a polymer of a light brown color which quickly dilutes in water in its entirety. The characteristic viscosity was measured for the produced polymer, i.e., sample 4: [η]=0.13 which corresponds to a molar weight Mw—13500, i.e., for the first time a polymer based on guanidine hydrochloride with such a high molar mass was produced by means of polycondensation.

According to the data from the analysis of the separate elements the produced polymer product polyoxyethylene guanidine hydrochloride corresponds to the above mentioned polyoxyethylene structured group.

It was determined in %: C-53.1; H-7.85; N-6.95.
It was calculated in %: C-52.3; H-7.87; N-7.04.

The produced polymer is provided with a lower toxicity and an increased bactericidity (see table.) The produced polymer is also provided with the distinct characteristic of a surface-active polymer.

It has been shown that the value of the surface tension 32 din/ch determined for this sample comes close to the surface tension of the known surface-active substance dodecyle-sodiumsulfate. (It must be stressed that no distinct surface-active characteristics could be determined in the PHMG-samples.) This characteristic of a surface-active substance should allow a more active occurrence of biocidal characteristics for syntheticized polymer products at the phase separation limit, specifically for the treatment (desinfection) of surfaces and their utilization as components in detergents.

EXAMPLE 5

Production of Polytriethylene Glycol-Guanidine Dihydrogen Phosphate.

In a three-necked piston having a capacity of 250 ml and being provided with a mechanical mixing device and an air cooler, 47.5 g (0.32 mol) liquid triethylene glycol diamine (relative molar mass 148) are inserted at room temperature. Subsequently, 50.24 g (0.32 mol) powdered guanidine dihydrogen phosphate (relative molar mass 157) is inserted into the piston, i.e., in the molar relation of the reagents 1:1. The piston with the liquid reaction mass is inserted into an oil-bath with a temperature regulator. The reaction mass is heated within of 11 hours to a temperature of 170° C., permanently being mixed. From the first minutes of the mentioned thermal regulation on, an intensive release of ammonia occurred (coloration of indicator papers) proving the process of the reaction of polycondensation. During the progression of the reaction, the reaction mass becomes thickened and a foam formation can be visually observed. The reaction mixture gradually changed into a resin having a white color with its volume exceeding the volume of the original liquid mixture. As soon as the release of ammonia gas is completed this reaction concludes as well. After the piston has cooled, the polymer resin is removed from the piston with the aid of a spatula and is ground into powder by means of a mortar, providing a higher hydrophoby in relation to polyoxytriethylene glycol guanidine hydrochloride, but simultaneously being quickly soluble in water. The experiment resulted in a yield of approximately 84.5 g of the final polymer product. The characteristic viscosity of the produced polymer was measured: 0.4 N in an aqueous sodiumchloride solution at 25° C. The viscosity is $[\eta]=0.056$ dl/g.

Analysis of the Elements of the Produced Polymer:
Calculated for $C_7N_3O_6PH_{18}$: C-30.99%, N-15.49%, O-35.42%, P-11.44%, H-6.64%
Discovered: C-31.38%, N-15.25%, P-11.67%, H-6.49%.
The analysis proves the consistency of the produced polymer with the required structure.

The biocidal characteristics of the produced polymer were examined. For two types of bacteria the value of the minimum inhibitive concentration in the unit ($\mu$g/ml) was determined. In case of *E-coli* bacteria the value is 2.1 $\mu$g/ml; in case of *Ps aeruginosa*—6.2 $\mu$g/ml. This confirms the high level of biocidal activity of the produced polymer. Some toxicological characteristic values of the polymer were examined as well, the value $LD_{50}$ (oral dose) for rats was determined. This value is 3200 mg/kg which proves the low toxicity of the polymer.

EXAMPLE 6

Production of Polytriethylene Glycol Guanidine Carbonate.
In a three-necked piston having a capacity of 1 l and being provided with a mechanical mixing device and an air cooler, 148 g (1 mol) liquid triethylene glycol diamine and, subsequently, 121 g (1 mol) powdered guanidine carbonate are inserted at room temperature.

Under permanent thorough mixing, the piston is heated in an oil bath; here, a rather homogenous mixing of the reagents occur. An intensive reaction with a release of ammonia starts at a temperature of 140° C. The original mixture is maintained at this temperature (140° C.) for the duration of 15 hours. Subsequently it thickens and transforms into a light yellow mass in the shape of a foam having a volume that considerably exceeds the volume of the original reaction mass. After the piston has cooled, the polymer resin is removed therefrom with the aid of a spatula and is ground in a mortar into a powder having a light color which is provided with a rather high level of hydrophoby. As a result of the experiment, approximately 232 g of a limitedly water-soluble polymer—polytriethylene glycol guanidine carbonate was produced having a characteristic viscosity of $[\eta]=0.065$ dl/g (measured at 25° C. in a 0.4 N aqueous NaCl-solution).

Analysis of the Elements of the Produced Polymer:
Calculated for $C_8N_3O_5H_{17}$: C-40.85%, N-17.87%, O-34.04%, H-7.23%
Discovered: C-41.31%, N-17.65%, H-7.03%.
The analysis proves that the results of the experiment correspond to the calculations as desired.

The value of minimum inhibition concentration ($\mu$g/ml) for *E-coli*-bacteria was determined for the produced polymer—polytriethylene glycol guanidine carbonate. The value of minimum inhibition concentration is 20 mg/ml confirming the biocidal activity of the produced polymer.

TABLE

| | Characteristics of synthetic polyoxyalkylene guanidine hydrochloride | | | |
|---|---|---|---|---|
| Sample No. | Characteristic viscosity $[\eta]$ = dl/g measured in 0.1 n NaCl-solution at 25° C. | Average weight of the relative molar mass- Mw = | Bactericidity minimum inhibition concentration in % (*E-coli*, stock 2590) | Toxicity, Oral dose $LD_{50}$ mg/kg (for rats) |
| Prototype | 0.1 | 10000 | 0.0007 | 2500 |
| 1 a) | 0.04 | 2500 | 0.003 | |
| 1 b) | 0.07 | 5800 | 0.0015 | |
| 1 c) | 0.085 | 9100 | 0.001 | 3000 |
| 2 | 0.11 | 11800 | 0.0003 | 3100 |
| 3 a) | 0.045 | 3000 | 0.002 | |
| 3 b) | 0.12 | 12500 | 0.0001 | 3150 |
| 4 | 0.13 | 13500 | 0.00007 | 3250 |

The invention claimed is:

1. A biocidal polymer guanidine derivative based on diamines which include two amino groups and oxyalkyl chains therebetween, wherein the guanidine derivatives are a product of a polycondensation of a guanidine acid addition salt with diamines which include polyoxyalkylene chains between two amino groups.

2. The biocidal polymer according to claim 1, in the form of a number of polyoxyalkylene guanidine salts which have triethylene glycol diamine (relative molecular mass 148), polyoxy propylene diamine (relative molar mass 230), and polyoxyethylene diamine (relative molar mass 600).

3. A process for producing polyoxyalkylene guanidine salts using diamines which are included between two amino groups in a liquid medium, wherein the liquid diamines are exposed to the polycondensation with guanidine salts in a medium of liquid diamine under permanent thorough mixing from the beginning to the completion of the reaction at an increased temperature and at the duration of the polycondensation of 9–16 hours depending of the diamine used.

4. The process according to claim 3, the polycondensation reaction is performed at an original mol ratio of the reagents of 1:1.

5. The process according to claim 3, wherein the polycondensation reaction is performed at temperatures between 140–190° C.

6. A process for producing polyoxyalkylene guanidine hydrochlorides, wherein the reaction of the polycondensation of guanidine hydrochloride and liquid diamines with the polyoxyalkylene group and the two amino groups occurs at an original mol ratio of reagents of 1:1 in a liquid reaction medium (in the medium of liquid diamine) under permanent thorough mixing from the beginning to the completion of the reaction at temperatures of 150–170° C. and at the duration of the polycondensation of 18–25 hours depending on the diamines used.

7. The process according to claim 6, wherein the reciprocal effect of guanidine hydrochloride with triethylene glycol diamine having a relative molar mass of 148 occurs at temperatures: from the beginning at 150° C. for the duration of 5 hours and subsequently at 170° C. for the duration of 13 hours, or at a temperature of 150° C. within of 25 hours.

8. The process according to claim 6, wherein the reciprocal effect of guanidine hydrochloride with polyoxypropylene diamine having a relative molar mass of 230 occurs at a temperature of 150° C. within of 2 hours and, subsequently, at a temperature of 170° C. within of 18 hours.

9. The process according to claim 6, wherein the reciprocal effect of guanidine hydrochloride occurs with polyoxyethylene dianiine having a relative molar mass of 600 at a temperature of 150° C. within of 25 hours.

* * * * *